US00PP24919P2

(12) United States Plant Patent
Beekenkamp

(10) Patent No.: US PP24,919 P2
(45) Date of Patent: Sep. 23, 2014

(54) ***DAHLIA* PLANT NAMED 'BKDAWHT'**

(50) Latin Name: *Dahlia hybrida*
Varietal Denomination: BKDAWHT

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 91 days.

(21) Appl. No.: 13/694,150

(22) Filed: Oct. 31, 2012

(51) Int. Cl.
*A01H 5/00* (2006.01)

(52) U.S. Cl.
USPC ..... Plt./321

(58) Field of Classification Search
USPC ..... Plt./321
See application file for complete search history.

*Primary Examiner* — Annette Para
(74) *Attorney, Agent, or Firm* — C. A. Whealy

(57) ABSTRACT

A new and distinct cultivar of *Dahlia* plant named 'BKDAWHT', characterized by its broadly upright and uniformly mounding plant habit; dense and bushy growth habit; dark green-colored leaves; long flowering period; double inflorescences with white-colored ray florets; and good garden performance.

2 Drawing Sheets

Botanical designation: *Dahlia hybrida.*
Cultivar denomination: 'BKDAWHT'.

BACKGROUND OF THE INVENTION

The present invention relates to a new and distinct cultivar of *Dahlia* plant, botanically known as *Dahlia hybrida* and hereinafter referred to by the name 'BKDAWHT'.

The new *Dahlia* plant is a product of a planned breeding program conducted by the Inventor in Maasdijk, The Netherlands. The objective of the breeding program is to create new container *Dahlia* plants that have a freely branching habit, attractive ray floret coloration, long flowering period and good garden performance.

The new *Dahlia* plant originated from an open-pollination in June, 2007 in Maasdijk, The Netherlands of a proprietary selection of *Dahlia hybrida* identified as code number 4000138, not patented, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled environment in Maasdijk, The Netherlands in July, 2008.

Asexual reproduction of the new *Dahlia* plant by cuttings in a controlled environment in Maasdijk, The Netherlands since November, 2008 has shown that the unique features of this new *Dahlia* plant are stable and reproduced true to type in successive generations.

SUMMARY OF THE INVENTION

Plants of the new *Dahlia* have not been observed under all possible environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAWHT'.

These characteristics in combination distinguish 'BKDAWHT' as a new and distinct *Dahlia* plant:

1. Broadly upright and uniformly mounding plant habit.
2. Dense and bushy growth habit.
3. Dark green-colored leaves.
4. Long flowering period.
5. Double inflorescences with white-colored ray florets.
6. Good garden performance.

Plants of the new *Dahlia* differ primarily from plants of the female parent selection in the following characteristics:

1. Plants of the new *Dahlia* are shorter than plants of the female parent selection.
2. Plants of the new *Dahlia* have smaller inflorescences than plants of the female parent selection.

Plants of the new *Dahlia* can be compared to plants of *Dahlia* 'Gallery Art Fair', disclosed in U.S. Plant Pat. No. 11,356. In side-by-side comparisons conducted in Maasdijk, The Netherlands, plants of the new *Dahlia* differed from plants of 'Gallery Art Fair' in the following characteristics:

1. Plants of the new *Dahlia* were shorter than plants of 'Gallery Art Fair'.
2. Plants of the new *Dahlia* had smaller inflorescences than plants of 'Gallery Art Fair'.

Plants of the new *Dahlia* can also be compared to plants of *Dahlia* 'BKDAWT', disclosed in U.S. Plant Pat. No. 11,356. In side-by-side comparisons conducted in Maasdijk, The Netherlands, plants of the new *Dahlia* differed from plants of 'BKDAWT' in the following characteristics:

1. Plants of the new *Dahlia* were shorter than plants of 'BKDAWT'.
2. Plants of the new *Dahlia* had darker green-colored leaves than plants of 'BKDAWT'.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'BKDAWHT' grown in a container.

The photograph on the second sheet is a close-up view of a typical inflorescence of 'BKDAWHT'.

DETAILED BOTANICAL DESCRIPTION

The aforementioned photographs and the following observations and measurements describe plants grown during the spring and early summer in 15-cm containers in a glass-covered greenhouse in Maasdijk, The Netherlands and under cultural practices which approximate those generally used in commercial *Dahlia* production. During the production of the plants, day and night temperatures ranged from 17° C. to 19° C. Plants were pinched one time and were 13 weeks old when the photographs and description were taken. In the following description, color references are made to The Royal Horticultural Society Colour Chart, 2007 Edition, except where general terms of ordinary dictionary significance are used.

Botanical classification: *Dahlia hybrida* 'BKDAWHT'.

Parentage:

*Female, or seed, parent*.—Proprietary selection of *Dahlia hybrida* identified as code number 4000138, not patented.

*Male, or pollen, parent*.—Unknown selection of *Dahlia hybrida*, not patented.

Propagation:

*Type*.—By terminal cuttings.

*Time to initiate roots, summer*.—About 16 days at temperatures ranging from 18° C. to 21° C.

*Time to initiate roots, winter*.—About 19 days at temperatures ranging from 18° C. to 21° C.

*Time to produce a rooted young plant, summer*.—About 21 days at temperatures ranging from 18° C. to 21° C.

*Time to produce a rooted young plant, winter*.—About 23 days at temperatures ranging from 18° C. to 21° C.

*Root description*.—Medium in thickness, fibrous; white in color; tuber development has not been observed on plants of the new *Dahlia*.

*Rooting habit*.—Moderate branching; medium density.

Plant description:

*Plant and growth habit*.—Broadly upright and mounding plant form; broad inverted triangle; about three primary lateral branches with numerous secondary branches developing per plant; inflorescences held above the foliar plane on strong peduncles; bushy and dense growth habit.

*Plant height*.—About 24.1 cm.

*Plant diameter or spread*.—About 29.5 cm.

*Lateral branches*.—Length: About 11.5 cm. Diameter: About 7 mm. Internode length: About 2.8 cm. Aspect: About 20° from vertical. Strength: Strong. Texture: Smooth, glabrous. Color: Close to 144A.

Foliage description:

*Arrangement*.—Leaves opposite and compound with three, five or seven leaflets; lower leaves with seven leaflets and upper leaves with three leaflets.

*Length*.—Leaves: About 14 cm. Terminal leaflets: About 9.5 cm. Lateral leaflets: About 6.4 cm.

*Width*.—Leaves: About 13.5 cm. Terminal leaflets: About 5.2 cm. Lateral leaflets: About 3.6 cm.

*Shape*.—Leaves, overall: Broadly ovate. Terminal and lateral leaflets: Ovate.

*Apex, leaflets*.—Acuminate.

*Base, leaflets*.—Attenuate.

*Margin, leaflets*.—Coarsely serrate to dentate.

*Venation pattern, leaflets*.—Pinnate.

*Texture, upper and lower surfaces, leaflets*.—Smooth, glabrous.

*Color*.—Developing leaflets, upper surface: Close to 144A; towards the apex, close to 137A. Developing leaflets, lower surface: Close to 144A. Fully expanded leaflets, upper surface: Between N137A and 147A; venation, close to 146A to 146B. Fully expanded leaflets, lower surface: Close to 147B; venation, close to 147B.

*Petioles*.—Length: About 3 cm. Width: About 5 mm. Height: About 4 mm. Texture, upper and lower surfaces: Smooth, glabrous. Color, upper surface: Close to 144A to 144B. Color, lower surface: Close to 144A.

Inflorescence description:

*Appearance and arrangement*.—Double inflorescence form with ray and disc florets forming acropetally on a receptacle; inflorescences positioned above and beyond the foliar plane on strong peduncles; terminal inflorescences face upright and axillary inflorescences face outwardly; freely flowering habit with about 18 inflorescences developing per plant.

*Fragrance*.—Faint, sweet.

*Flowering response and flowering period*.—Early flowering habit, plants begin flowering about 64 days after planting; long flowering period, plants flower continuously throughout the summer in The Netherlands.

*Post-production longevity*.—Inflorescences maintain good substance for about two to three weeks on the plant; inflorescences not persistent.

*Inflorescence buds*.—Height: About 6 mm. Diameter: About 1.3 cm. Shape: Flattened globular. Color: Between 144A and N144A to N144B.

*Inflorescence size*.—Diameter: About 8.5 cm. Depth (height): About 5.9 cm. Disc diameter: About 4 mm, inconspicuous. Receptacle height: About 4 mm. Receptacle diameter: About 7 mm. Receptacle color: Close to 145D.

*Ray florets*.—Quantity per inflorescence: About 150 arranged in about eight whorls. Length: About 3.2 cm. Width: About 1.7 cm. Shape: Elliptic. Apex: Broadly acute. Base: Cuneate. Margin: Entire. Aspect: Upright to roughly horizontal; ray florets carinate. Texture, upper surface: Smooth, glabrous; velvety. Texture, lower surface: Smooth, glabrous; slightly velvety. Color: When opening, upper and lower surfaces: Close to NN155A; towards the base, close to 150C. Fully opened, upper surface: Close to NN155A to NN155B; towards the base, close to 150C. Fully opened, lower surface: Close to NN155B; towards the base, close to 150C.

*Disc florets*.—Quantity per inflorescence: About 20 massed at the center of the inflorescence. Length: About 6 mm. Diameter: About 1 mm. Shape: Tubular, elongated; apices, acute. Texture, inner and outer surfaces: Smooth, glabrous. Color, when opening and fully opened, inner surface: Close to N167C; towards the apex, close to 9C; towards the base, close to 154A. Color, when opening and fully opened, outer surface:

Close to N167C; towards the apex, close to 9C; towards the base, close to 154A.

*Phyllaries*.—Quantity per inflorescence: About five arranged in a single whorl. Length: About 1.9 cm. Width: About 1 cm. Shape: Ovate. Apex: Broadly acute. Base: Cuneate. Margin: Entire. Texture, upper and lower surfaces: Smooth, glabrous. Color, upper surface: Close to N137C. Color, lower surface: Close to 137A.

*Peduncles*.—Length, terminal peduncle: About 6 cm. Length, axillary peduncle: About 8.9 cm. Diameter: About 2.5 mm. Aspect: Terminal peduncles, erect; axillary peduncles, about 30° from stem. Strength: Strong. Texture: Smooth, glabrous. Color: Close to 144A.

*Reproductive organs*.—Androecium, present on disc florets only: Quantity per floret: About four. Filament length: About 1 mm. Filament color: Close to 150D. Anther shape: Lanceolate. Anther length: About 4 mm. Anther color: Close to 7A. Pollen amount: Moderate. Pollen color: Close to 22A. Gynoecium, present on ray and disc florets: Quantity per floret: One. Pistil length: About 6 mm. Style length: About 5 mm. Style color: Close to 1C; towards the base, close to NN155D. Stigma shape: Cleft. Stigma color: Close to 12B. Ovary color: Close to 150D. Seeds and fruits: Seed and fruit development have not been observed on plants of the new *Dahlia*.

Disease & pest resistance: Plants of the new *Dahlia* have not been shown to be resistant to pathogens and pests common to *Dahlia* plants.

Garden performance: Plants of the new *Dahlia* have been observed to have good garden performance and to tolerate wind, rain and high temperatures of about 35° C. and to be hardy to USDA Hardiness Zone 8.

It is claimed:

1. A new and distinct *Dahlia* plant named 'BKDAWHT' as illustrated and described.

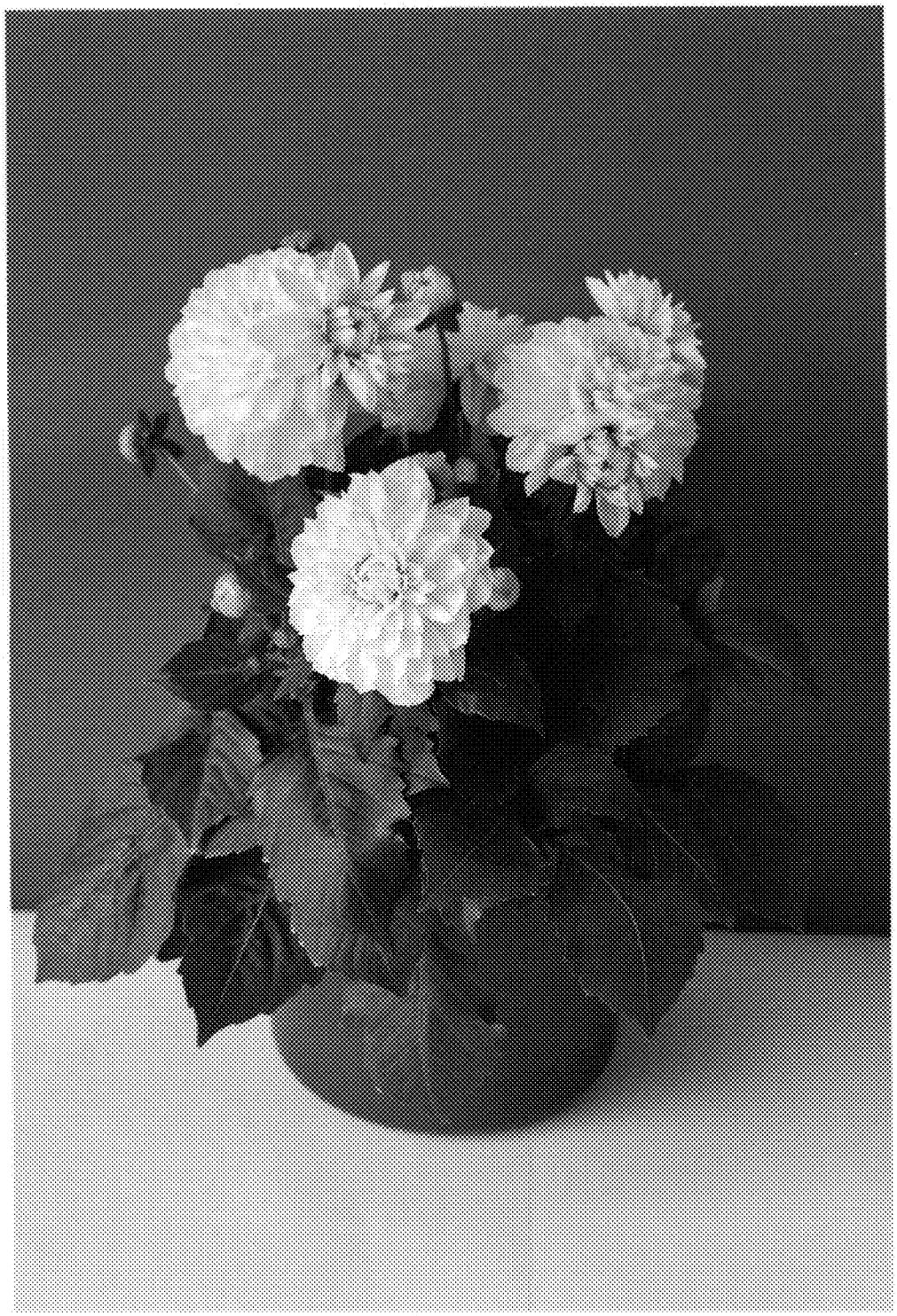

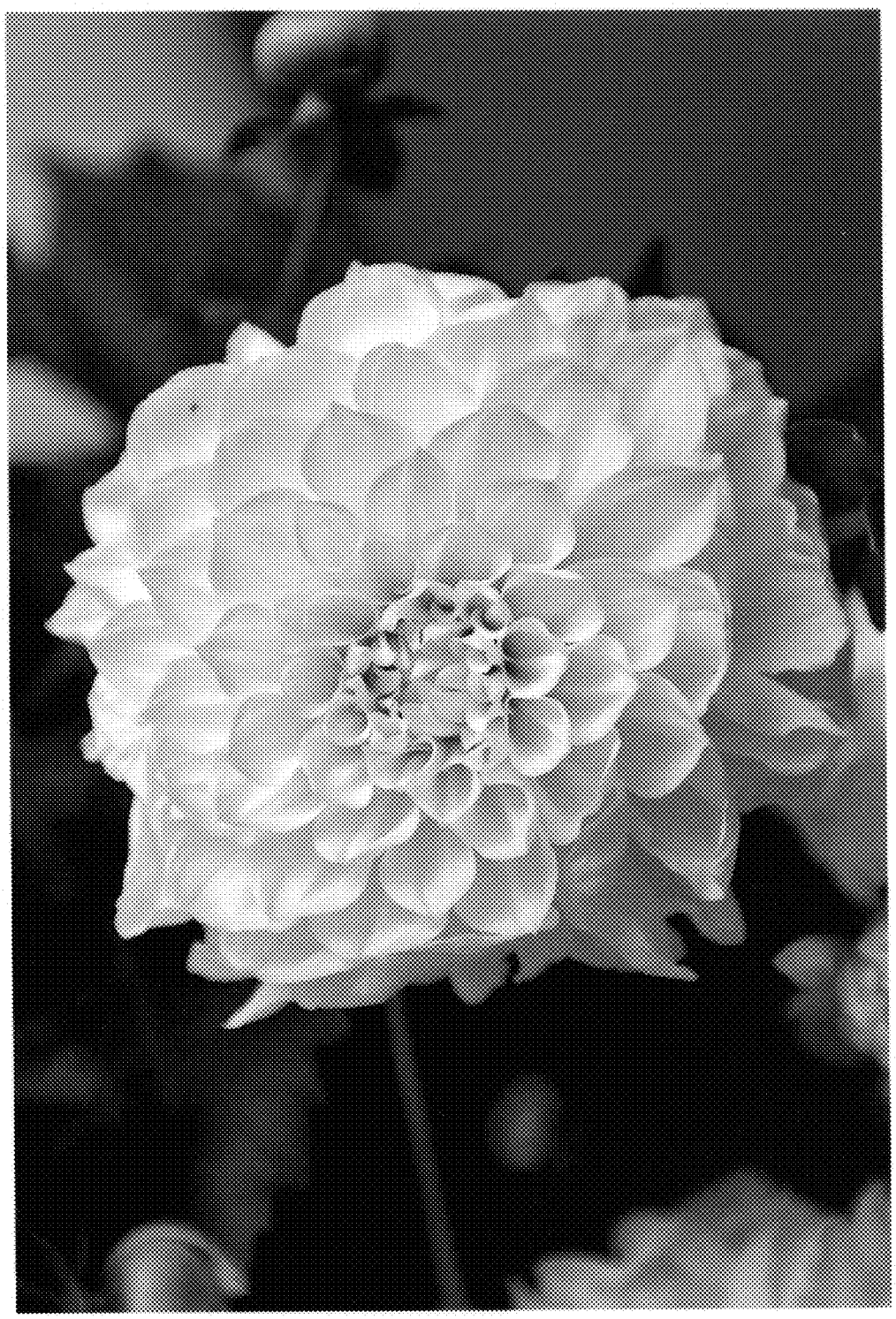

* * * * *